US010499795B2

(12) United States Patent
Ogawa et al.

(10) Patent No.: US 10,499,795 B2
(45) Date of Patent: Dec. 10, 2019

(54) ENDOSCOPIC-TREATMENT-INSTRUMENT OPERATION INPUT DEVICE

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/002,518

(22) Filed: Jan. 21, 2016

(65) Prior Publication Data
US 2016/0128773 A1 May 12, 2016

Related U.S. Application Data

(63) Continuation of application No. PCT/JP2014/069000, filed on Jul. 17, 2014.

(30) Foreign Application Priority Data

Jul. 26, 2013 (JP) ................. 2013-155887

(51) Int. Cl.
*A61B 1/00* (2006.01)
*A61B 34/00* (2016.01)
*A61B 17/00* (2006.01)
*A61B 17/29* (2006.01)
*A61B 17/34* (2006.01)
*A61B 18/00* (2006.01)

(52) U.S. Cl.
CPC ........ *A61B 1/00133* (2013.01); *A61B 1/0016* (2013.01); *A61B 1/00066* (2013.01);
(Continued)

(58) Field of Classification Search
CPC ............ A61B 1/00066; A61B 1/00068; A61B 1/0008; A61B 1/00101; A61B 1/00121;
(Continued)

(56) References Cited

U.S. PATENT DOCUMENTS

2002/0103418 A1 8/2002 Maeda et al.
2004/0054254 A1 3/2004 Miyake
(Continued)

FOREIGN PATENT DOCUMENTS

CN 1957836 A 5/2007
EP 1 782 744 A2 5/2007
(Continued)

OTHER PUBLICATIONS

Japanese Office Action dated Mar. 28, 2017 in Japanese Patent Application No. 2013-155887, together with an English language translation.
(Continued)

*Primary Examiner* — Ryan N Henderson
(74) *Attorney, Agent, or Firm* — Scully, Scott, Murphy & Presser, P.C.

(57) ABSTRACT

Provided is an endoscopic-treatment-instrument operation input device that includes: a grip section that is shaped so as to be capable of being gripped by the palm and at least the little finger and the ring finger of one hand of an operator; an operation section that is arranged at a position so as to be operable by the thumb of the one hand in state where the grip section is being gripped and that allows an operation command for causing a joint of the treatment instrument to actuate to be input; and a frictional fixing section that presses, and fixes in place with friction, a position midway along elongated trunk section of the treatment instrument in the longitudinal direction through use of the index finger of the one hand.

27 Claims, 22 Drawing Sheets

(52) U.S. Cl.
CPC ........ *A61B 17/00234* (2013.01); *A61B 17/29* (2013.01); *A61B 17/2909* (2013.01); *A61B 34/70* (2016.02); *A61B 34/74* (2016.02); *A61B 1/00147* (2013.01); *A61B 2017/00212* (2013.01); *A61B 2017/00398* (2013.01); *A61B 2017/00424* (2013.01); *A61B 2017/00469* (2013.01); *A61B 2017/2908* (2013.01); *A61B 2017/347* (2013.01); *A61B 2018/0091* (2013.01); *A61B 2034/742* (2016.02)

(58) Field of Classification Search
CPC . A61B 1/00133; A61B 1/0014; A61B 1/0016; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 34/74; A61B 17/2909; A61B 2017/0046; A61B 2017/00464; A61B 2017/00469; A61B 2017/00473; A61B 2017/0042; A61B 2017/00424
USPC ....... 600/104, 106, 107, 114, 115, 127, 129, 600/131, 139–152
See application file for complete search history.

(56) References Cited

U.S. PATENT DOCUMENTS

| | | | |
|---|---|---|---|
| 2007/0100201 A1 | 5/2007 | Komiya et al. | |
| 2008/0208002 A1* | 8/2008 | Maruyama | A61B 1/0052 600/131 |
| 2008/0262293 A1* | 10/2008 | Murakami | A61B 1/0052 600/102 |
| 2009/0018390 A1 | 1/2009 | Honda et al. | |
| 2009/0112060 A1 | 4/2009 | Sugiyama et al. | |
| 2012/0209067 A1* | 8/2012 | Hosaka | A61B 1/00048 600/109 |

FOREIGN PATENT DOCUMENTS

| | | |
|---|---|---|
| EP | 1 982 637 A1 | 10/2008 |
| EP | 2 014 218 A2 | 1/2009 |
| JP | H05-192348 A | 8/1993 |
| JP | 2005-131373 A | 5/2005 |
| JP | 2005-537865 A | 12/2005 |
| JP | 2007-125180 A | 5/2007 |
| JP | 2008-264517 A | 11/2008 |
| JP | 2009-011809 A | 1/2009 |
| JP | 2009-101077 A | 5/2009 |

OTHER PUBLICATIONS

International Search Report dated Aug. 12, 2014 issued in PCT/JP2014/069000.
Extended Supplementary European Search Report dated Feb. 10, 2017 in related European Patent Application No. 14 82 9298.0.
European Patent Office Communication dated Jan. 29, 2019 in corresponding European Patent Application No. 14 829 298.0.

* cited by examiner

ENDOSCOPIC-TREATMENT-INSTRUMENT OPERATION INPUT DEVICE

CROSS-REFERENCE TO RELATED APPLICATIONS

This is a continuation of International Application PCT/JP2014/069000, with an international filing date of Jul. 17, 2014, which is hereby incorporated by reference herein in its entirety. This application claims the benefit of Japanese Patent Application No. 2013-155887, the content of which is incorporated herein by reference.

TECHNICAL FIELD

The present invention relates to an endoscopic-treatment-instrument operation input device.

BACKGROUND ART

A joystick or an operation switch that is attached to a joint-driving motor unit fixed to the base end of a treatment instrument are known conventional examples of an operation input device for an electrical treatment instrument that has a joint at the distal end thereof and is introduced inside a body via a instrument channel of an endoscope (refer to PTLs 1 and 2, for example). The operation input devices described in PTLs 1 and 2 are fixed to the base end of the treatment instrument, and therefore, the operator operates the joystick while moving the elongated treatment instrument forward and backward in the longitudinal axis direction of the treatment instrument or while twisting the treatment instrument around the longitudinal axis using one hand holding the motor unit at the base end.

CITATION LIST

Patent Literature

{PTL 1} Japanese Unexamined Patent Application Publication No. 2009-101077
{PTL 2} Japanese Unexamined Patent Application Publication No. Hei 5-192348

SUMMARY OF THE INVENTION

Technical Problem

In order to achieve the above-described object, the present invention provides the following solutions.

An aspect of the present invention is an endoscopic-treatment-instrument operation input device for operating a treatment instrument that has a joint at a distal end of elongated trunk section to be introduced via a channel of an endoscope, the operation input device including: a grip section shaped so as to be capable of being gripped by a palm and at least a little finger and a ring finger of one hand of an operator; an operation section that is arranged at a position so as to be operable by a thumb of the gripping hand in a state where the grip section is being gripped and that allows an operation command for causing the joint to actuate to be input; and a frictional fixing section that presses, and fixes in place with friction, the trunk section at a position midway along the trunk section in a longitudinal direction of the trunk section through use of an index finger of the gripping hand in a state where the grip section is being gripped.

DESCRIPTION OF EMBODIMENTS

An operation input device (endoscopic-treatment-instrument operation input device) 1 according to an embodiment of the present invention will be described hereafter with reference to the drawings.

Figure 1:
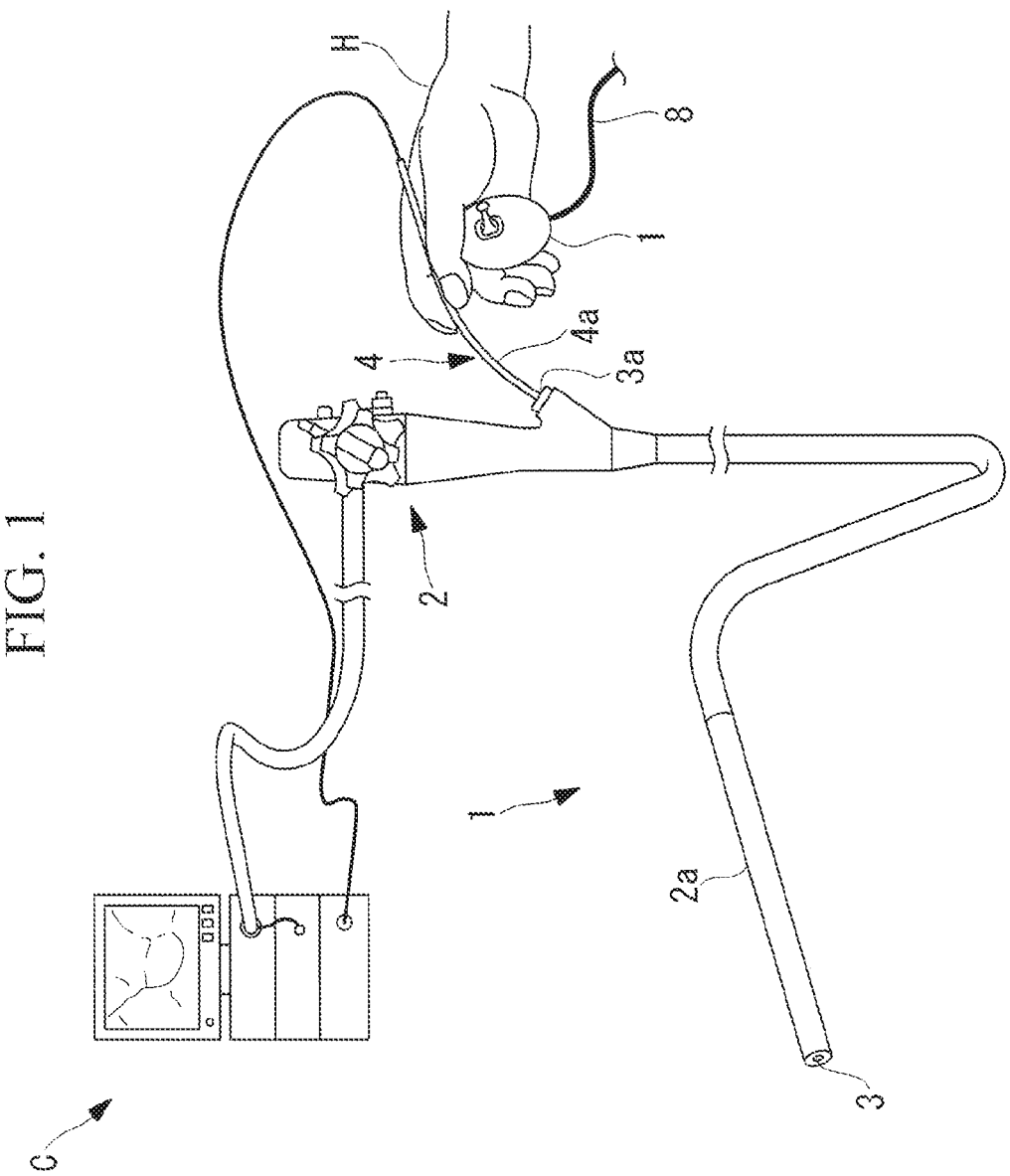
FIG. 1 is an overall configuration view for describing the operation of a treatment instrument employing an endoscopic-treatment-instrument operation input device according to an embodiment of the present invention.
Figure 2:
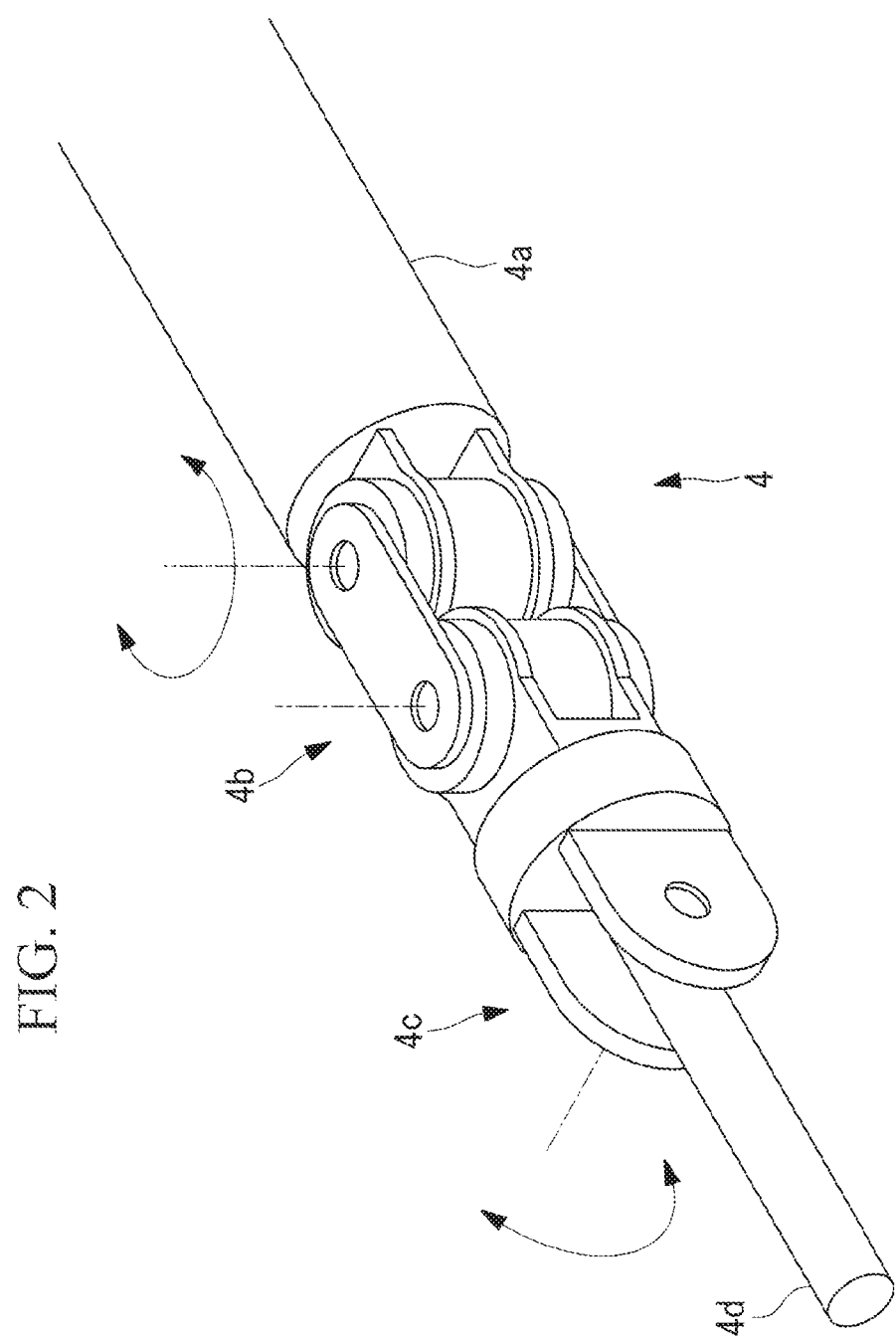
FIG. 2 is a perspective view illustrating an example of a distal end of the treatment instrument in FIG. 1.

As illustrated in FIG. 1, the operation input device 1 according to this embodiment is a device for making a treatment instrument 4 that is introduced into a instrument channel 3 of an endoscope 2 function. The treatment instrument 4 is provided with a trunk section 4*a* that is sufficiently longer than an insertion section 2*a* of the endoscope 2 and possesses elasticity, and as illustrated in FIG. 2 has two joints 4*b* and 4*c*, which can bend within planes orthogonal to each other, and an end effector 4*d* at a distal end of the trunk section 4*a*, which is made to protrude from a distal end surface of the insertion section 2*a* of the endoscope 2.

Figure 3A:
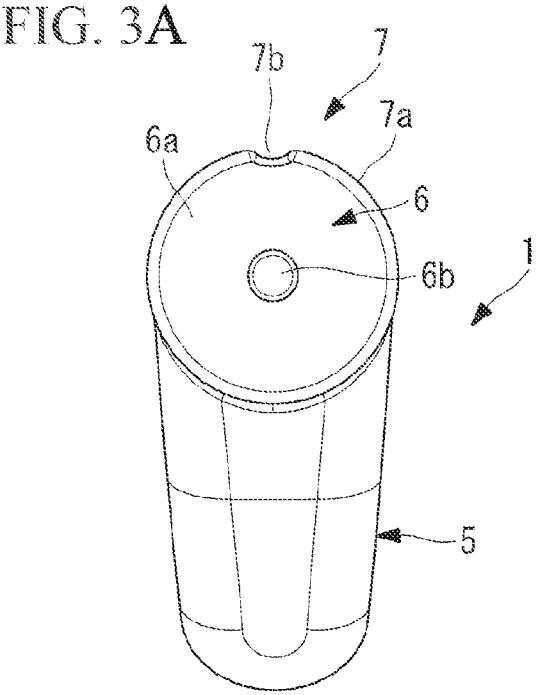
FIG. 3A is a front view illustrating the endoscopic-treatment-instrument operation input device according to the embodiment of the present invention.
Figure 4A:
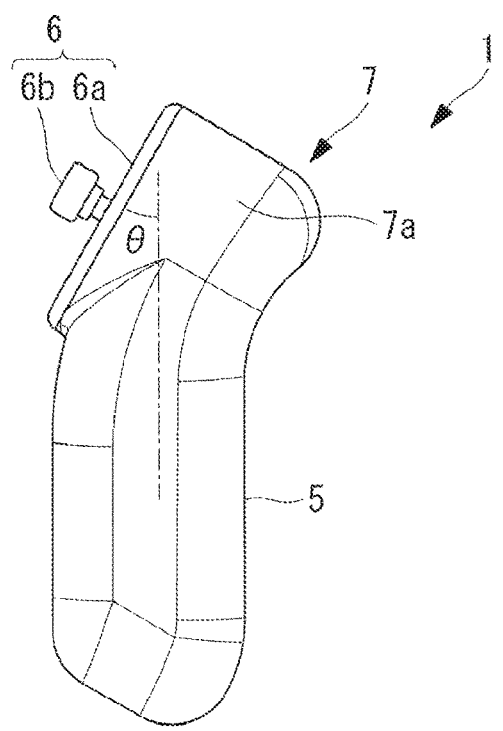
FIG. 4A is a side view of the endoscopic-treatment-instrument operation input device in FIG. 3A.

As illustrated in FIGS. 3A and 4A, the operation input device 1 according to this embodiment is provided with a grip section 5 that can be gripped by one hand H of an operator and that has rounded edges, an operation section 6 that is arranged at one end of the grip section 5, and a frictional fixing section 7 that is arranged on an edge surface of the operation section 6.

Figure 3B:
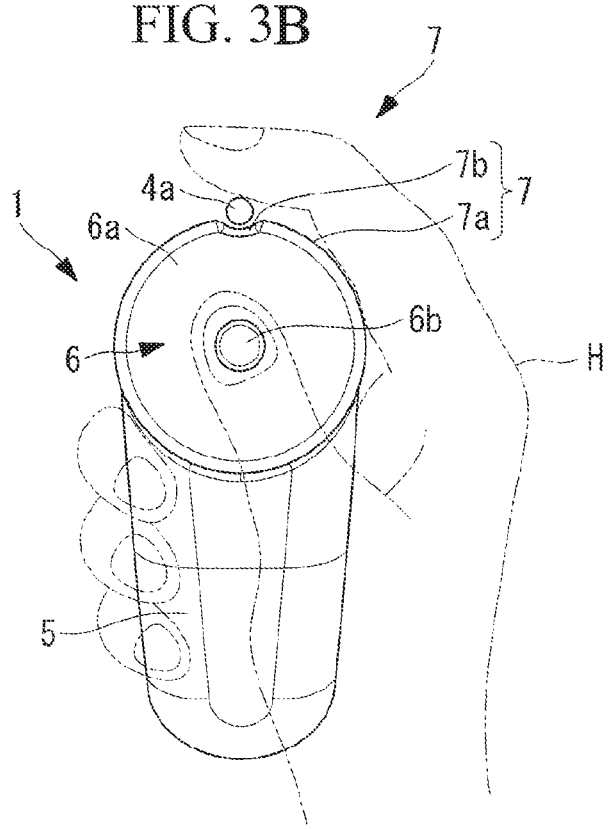
FIG. 3B is a front view that illustrates the endoscopic-treatment-instrument operation input device in FIG. 3A together with a hand gripping the same.

As illustrated in FIG. 3B, the grip section 5 is formed in such a shape that, when the operator holds the grip section 5 in the palm of the one hand H, the grip section 5 is enclosed by the palm, the little finger and the ring finger (little finger to middle finger depending on the case) of the holding hand H, and the outer peripheral surface thereof fits perfectly to the surface of the hand from the palm to the fingers and is unlikely to fall. The grip section 5 has a gently tapering shape that tapers toward the side opposite to the end portion where the operation section 6 is provided. Thus, when the grip section 5 is gripped such that the operation section 6 faces upward, the grip section 5 tapers downward, thus realizing such a shape that the surface of the grip section 5 is made to closely contact the surfaces of the palm and fingers by gravity, the feeling of achieving a fit is increased, and the grip section 5 is unlikely to slip out.

Figure 4B:
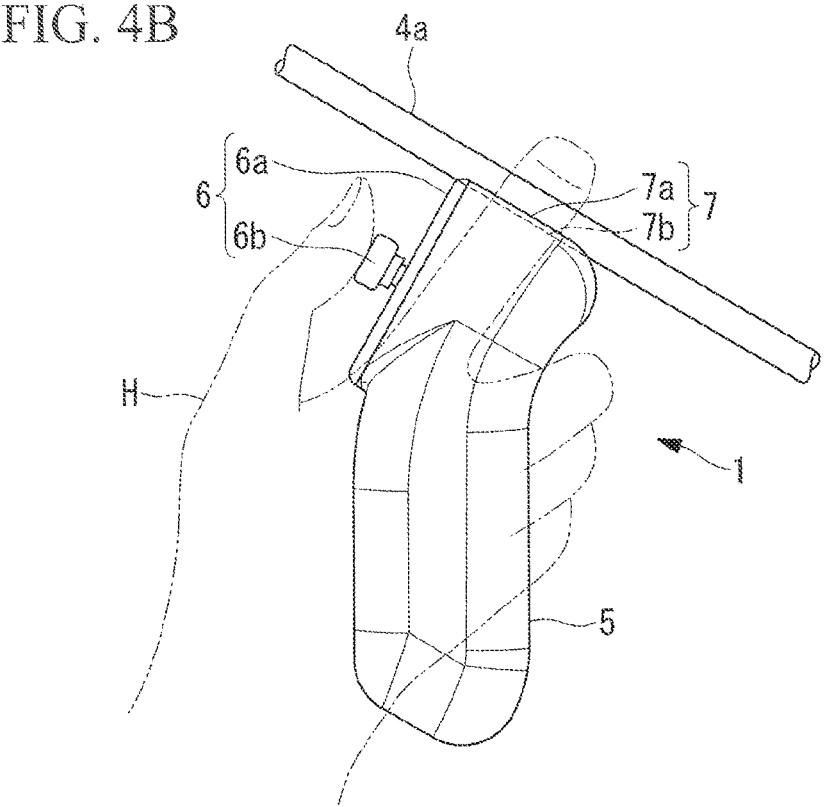
FIG. 4B is a side view of the endoscopic-treatment-instrument operation input device in FIG. 4A and also illustrates a hand gripping the same.

As illustrated in FIG. 4A, the operation section 6 includes a joystick 6*b* that stands upright in substantially the center of a substantially circular flat part 6*a*, which is inclined with respect to the longitudinal axis of the grip section 5. The flat part 6*a* is gently inclined at an angle θ with respect to the longitudinal axis from an outer peripheral surface of the grip section 5 toward one end in a direction toward the center of the grip section 5. Thus, as illustrated in FIG. 4B, when the operator grips the grip section 5 using the palm, little finger, and ring finger of the one hand H, the thumb is comfortably positioned in a direction along the flat part 6*a*, and the pad of the thumb is arranged at a position over the tip of the joystick 6*b*.

With the joystick 6*b*, it is possible to select the joints 4*b* and 4*c* and the bending directions of the joints 4*b* and 4*c*, which are caused to actuate in accordance with a tilting direction of the joystick 6*b* from a neutral position where the joystick 6*b* stands erect in substantially the center of the flat part 6*a*, and it is possible to input command signal for setting a bending angle of the joints 4*b* and 4*c* in accordance with a tilting angle of the joystick 6*b* from the neutral position. The command signal input by using the joystick 6*b* is transmitted to an external controller C via a wiring line 8 or via wireless communication, and the joints 4*b* and 4*c* of the treatment instrument 4 are actuated on the basis of an output of the controller C.

Figure 3C:
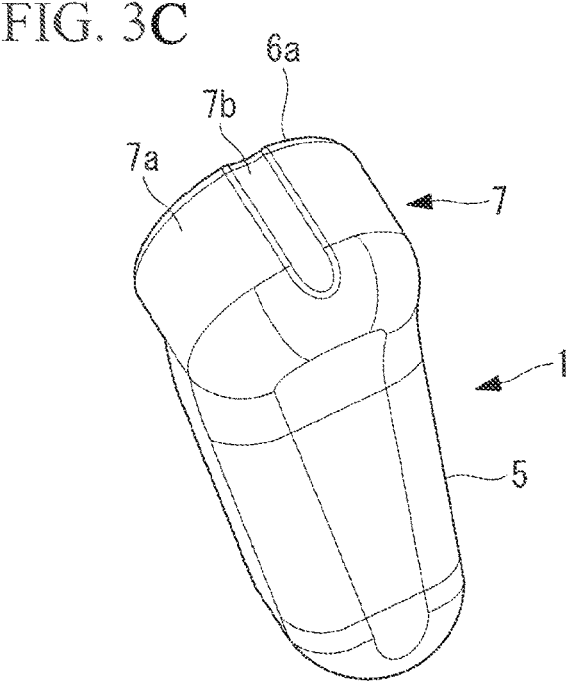
FIG. 3C is a perspective view in which the endoscopic-treatment-instrument operation input device in FIG. 3A is seen from a frictional fixing section.

The frictional fixing section 7 includes a groove 7*b* that is provided in a semi-cylindrical surface 7*a*, which is disposed along the outer periphery of the substantially circular flat part 6*a* of the operation section 6, and extends in the direction of a generating line substantially in the center of the semi-cylindrical surface 7*a*, as illustrated in FIG. 3C. The groove 7*b* has an inner wall surface made up of the inner surface of part of a cylinder having a certain radius. The trunk section 4*a* of the treatment instrument 4 has a substantially circular cross-sectional shape, and the groove 7*b* has an inner diameter that is larger than the outer diameter of the trunk section 4*a*.

As illustrated in FIG. 3B, the arranged semicylindrical surface 7*a* of the frictional fixing section 7 is arranged at a position where the index finger is naturally positioned in a circumferential direction when the grip section 5 is gripped by the palm, the little finger, and the ring finger, and the thumb is arranged on the operation section 6. As illustrated in FIG. 3C, the groove 7*b* is arranged in substantially the center of the semicylindrical surface 7*a* in the circumferential direction, extends in a direction that intersects the length direction of the index finger of the gripping hand H, and is at a position in the vicinity of the first joint of the index finger.

The operation of the thus-structured operation input device 1 according to this embodiment will be described below.

As illustrated in FIGS. 3B and 4B, in order to move the treatment instrument 4 in the longitudinal direction of the trunk section 4*a* and rotate the treatment instrument 4 around the longitudinal axis of the trunk section 4*a* while operating the joints 4*b* and 4*c* of the treatment instrument 4 by using the operation input device 1 according to this embodiment, the operator who is to operate the endoscope 2 grips the grip section 5 with one hand, for example, with the palm and the little finger to the middle finger of the right hand H, operates the operation section 6 using the thumb of the right hand H and presses the trunk section 4a against the inner surface of the groove 7b with the index finger of the right hand H in a state where the trunk section 4a of the treatment instrument 4 is arranged along the groove 7b of the frictional fixing section 7.

The operation input device 1 is thus fixed to the trunk section 4a by the friction between the inner surface of the groove 7b and the trunk section 4a, and therefore, the operator can perform an operation in which the trunk section 4a of the treatment instrument 4 is moved in the longitudinal direction of the trunk section 4a and an operation in which the trunk section 4a is twisted around the longitudinal axis of the trunk section 4a with the right hand H that grips the operation input unit 1. In this case, in contrast to a conventional treatment instrument, the operation input device 1 according to this embodiment is not fixed to the base end of the trunk section 4a and therefore can be operated by being fixed at a position midway along the trunk section 4a in the longitudinal direction.

Consequently, an operator who is familiar with conventional endoscope techniques for operating a hand-operated treatment instrument can perform pushing/pulling and twisting operations by gripping the trunk section 4a of the treatment instrument 4 in the vicinity of an introduction opening 3a leading to the instrument channel 3 of the endoscope 2, as in the technique that the operator is familiar with. As a result, compared with the conventional case where an operation is performed at the base end of the trunk section 4a, which is a long way from the introduction opening 3a to the instrument channel 3, there is an advantage in that buckling or kinking of the trunk section 4a is unlikely to occur, and an operational force can be transferred with more certainty to the distal end of the treatment instrument 4.

In the operation input device 1 according to this embodiment, the inner diameter of the groove 7b is formed so as to be larger than the outer diameter of the trunk section 4a of the treatment instrument 4, and therefore the trunk section 4a can be satisfactorily accommodated inside the groove 7b, and the integrity of the trunk section 4a can be maintained as a result of the corners of the edges of the groove 7b being prevented from pressing against the trunk section 4a.

In addition, in the case where an operation section that is provided in a driving section is operated by gripping the driving section as in the conventional case, a heavy driving source, such as a motor, accommodated inside the driving section, has had to be supported. In contrast, with the operation input device 1 according to this embodiment, the operation section is provided separately from a driving source for driving the joints 4b and 4c, and therefore, the weight supported by the operating hand H can be significantly reduced, and consequently, reduced exertion can be realized and the ease of performing precision operations can be improved in lengthy operations, which are desirable for an operation section to be used in operations.

Furthermore, with the operation input device 1 according to this embodiment, the trunk section 4a of the treatment instrument 4, which is clamped between the index finger and the groove 7b, extends in a direction substantially orthogonal to the flat part 6a of the operation section 6, as illustrated in FIG. 4B, and therefore, the joystick 6b can be tilted in a direction that intersects the longitudinal direction of the trunk section 4a. As a result, there is an advantage in that the actuation directions of the joints 4b and 4c at the distal end of the trunk section 4a, the joints 4b and 4c pivoting around axes that intersect the length direction of the trunk section 4a, and the tilting directions of the joystick 6b can be easily matched to each other, and the joints 4b and 4c can be intuitively operated.

It is preferable that the trunk section 4a of the treatment instrument 4 be substantially orthogonal to the flat part 6a of the operation section 6, but there may be an angle between the trunk section 4a and the flat part 6a so long as the angle is within the range of an acute angle that allows a person to convert the coordinate system without there being a large feeling of unnaturalness.

Figure 5:
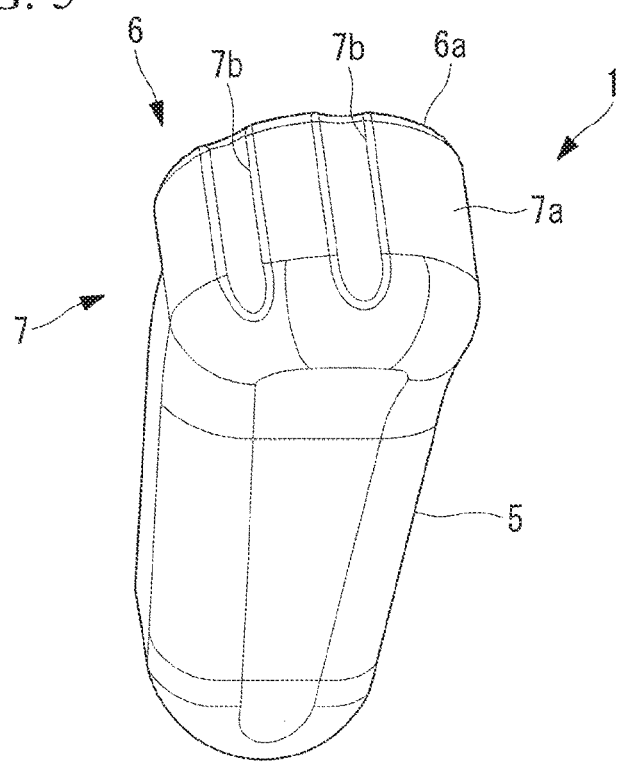
FIG. 5 is a perspective view seen from a frictional fixing section and illustrates a first modification of the endoscopic-treatment-instrument operation input device in FIG. 3A.

In this embodiment, a single groove 7b has been exemplified for the frictional fixing section 7, but two or more grooves 7b may instead be provided in such a manner as to be spaced apart from each other in the circumferential direction of the semicylindrical surface 7a, as illustrated in FIG. 5. The position at which the trunk section 4a is easily clamped by the index finger differs depending on individual differences between operators, and therefore, an operator can clamp the trunk section 4a of the treatment instrument 4 by choosing the groove 7b that is at a position where clamping is easy. Although the groove 7b having an inner surface shaped like the inner surface of a cylinder has been exemplified, a flat surface such as that of a rectangular groove 7b may be provided instead. Furthermore, a configuration may be adopted in which the trunk section 4a is clamped between a position on a semicylindrical surface 7a that does not include the groove 7b, or the like, and the index finger.

Figure 6:
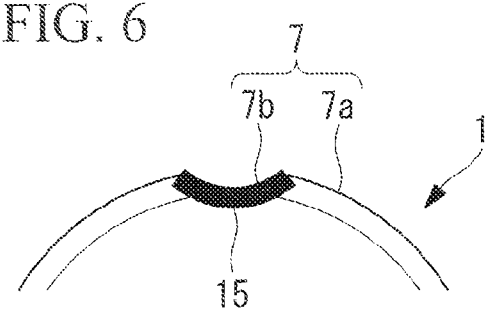
FIG. 6 is an enlarged view of part of the frictional fixing section and illustrates a second modification of the endoscopic-treatment-instrument operation input device in FIG. 3A.

In addition, as illustrated in FIG. 6, an anti-slip member (for example, a rubber member) 15 may be arranged on a surface that presses against the inner surface of the groove 7b or a side surface of the trunk section 4a. As a result, the operation section 6 can be maintained, with a little force, in a state in which it is fixed against the trunk section 4a, which is clamped between the index finger and the groove 7b, and operability can be improved.

Figure 7A:
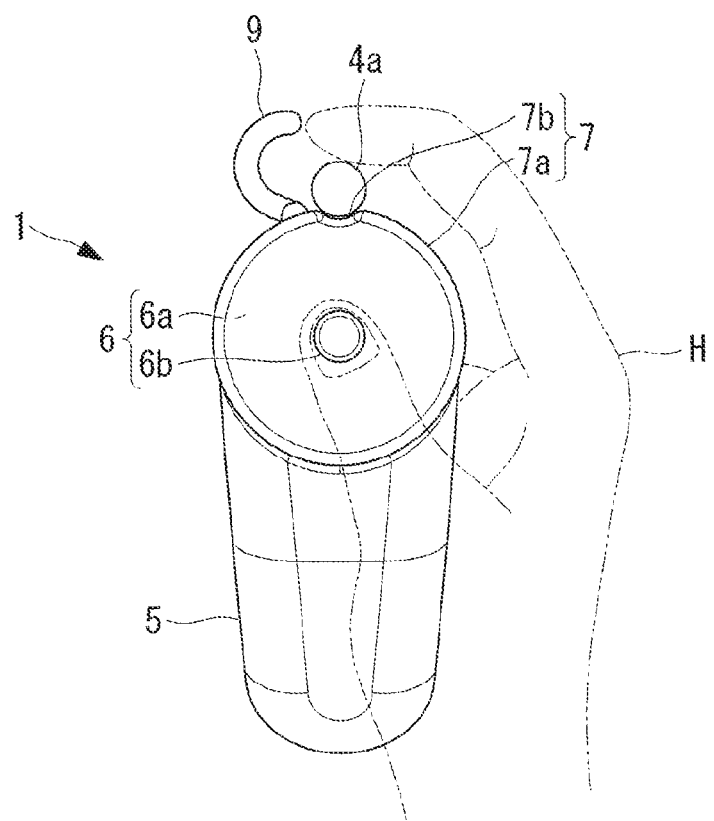
FIG. 7A is a front view of a third modification of the endoscopic-treatment-instrument operation input device in FIG. 3A and illustrates a state in which a clamping member is open.
Figure 7B:
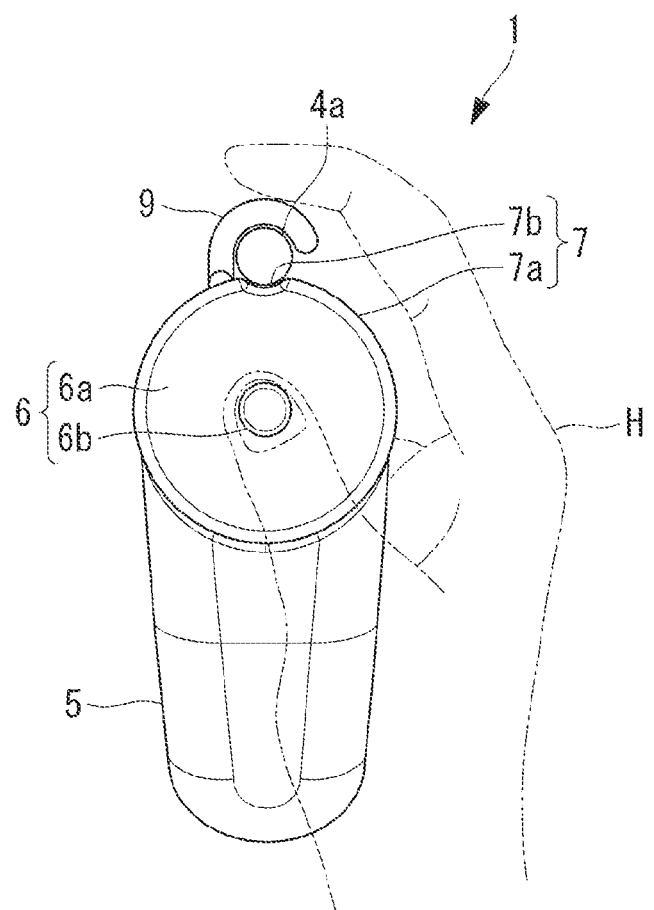
FIG. 7B is a front view of the endoscopic-treatment-instrument operation input device in FIG. 7A and illustrates a state in which the clamping member is closed.

Furthermore, in this embodiment, although a case has been exemplified and described in which the trunk section 4a of the treatment instrument 4 is directly pressed by the index finger of the hand H holding the grip section 5, a configuration may instead be adopted in which a clamping member 9 is provided so as to be able to move relatively between a position separated from the groove 7b, as illustrated in FIG. 7A and a position close to the groove 7b, as illustrated in FIG. 7B, and the trunk section 4a is clamped between the clamping member 9 and the groove 7b by moving the clamping member 9 with the index finger.

The load acting on the index finger can be reduced compared with the case where the trunk section 4a is directly clamped by the index finger, and the trunk section 4a of the treatment instrument 4 can be clamped with more certainty.

The clamping member 9 may be provided with an urging member (not illustrated) such as a spring for applying an urging force in a separation direction. The trunk section 4a of the treatment instrument 4 can be clamped between the clamping member 9 and the groove 7b by overcoming the urging force generated by the urging member and bringing the clamping member 9 closer to the groove 7b with the index finger, and the fixed state of the trunk section 4a can be released by removing the index finger from the clamping member 9 and allowing the urging member to cause the clamping member 9 to instantly separate from the trunk section 4a.

The clamping member 9 may have a mechanism that is locked in a state where the clamping member 9 has been moved to a position close to the groove 7b and is clamping the trunk section 4a against the groove 7b. Once the clamping member 9 has been put into a locked state, the index finger can be used for other purposes.

Figure 8A:
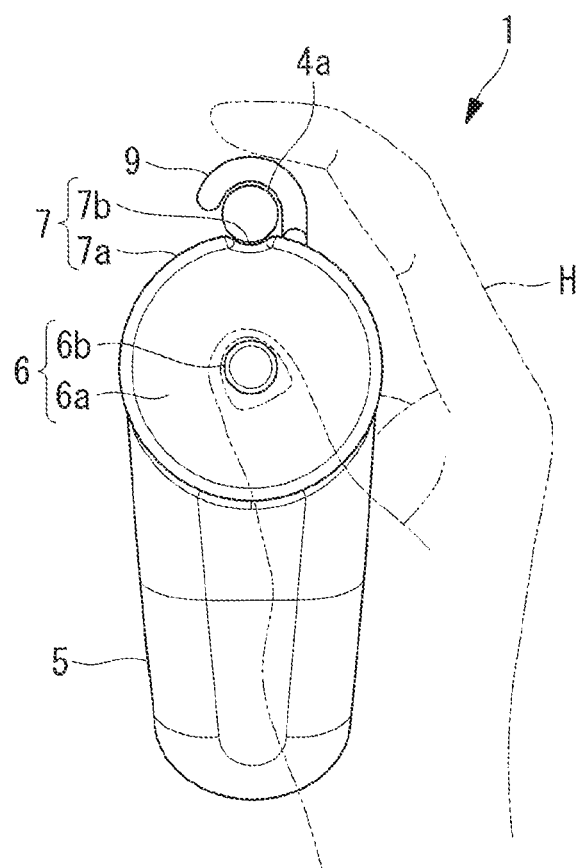
FIG. 8A is a front view illustrating a state in which a clamping member of the endoscopic-treatment-instrument operation input device, which is provided with a clamping member that swings in the opposite direction to the clamping member in FIG. 7A, is closed.
Figure 8B:
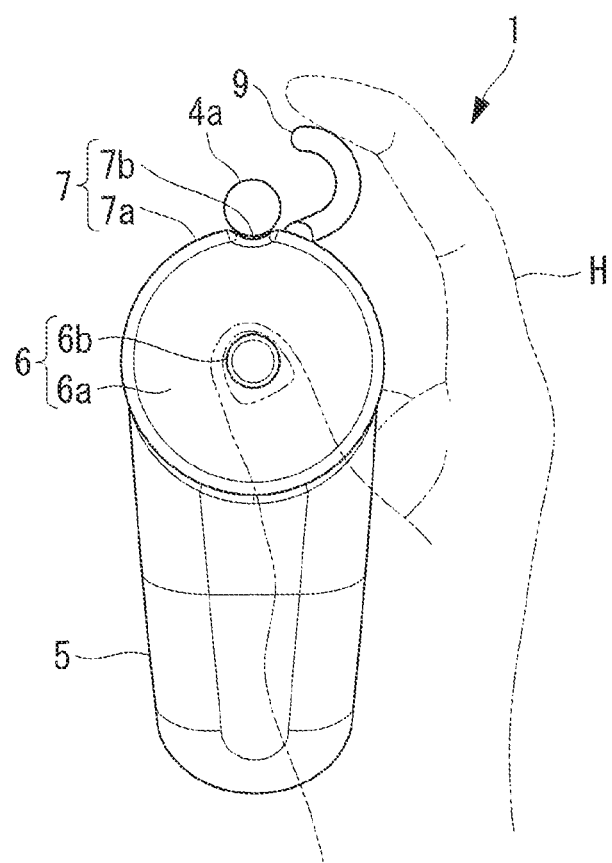
FIG. 8B is a front view of the endoscopic-treatment-instrument operation input device in FIG. 8A and illustrates a state in which the clamping member is open.
Figure 8C:
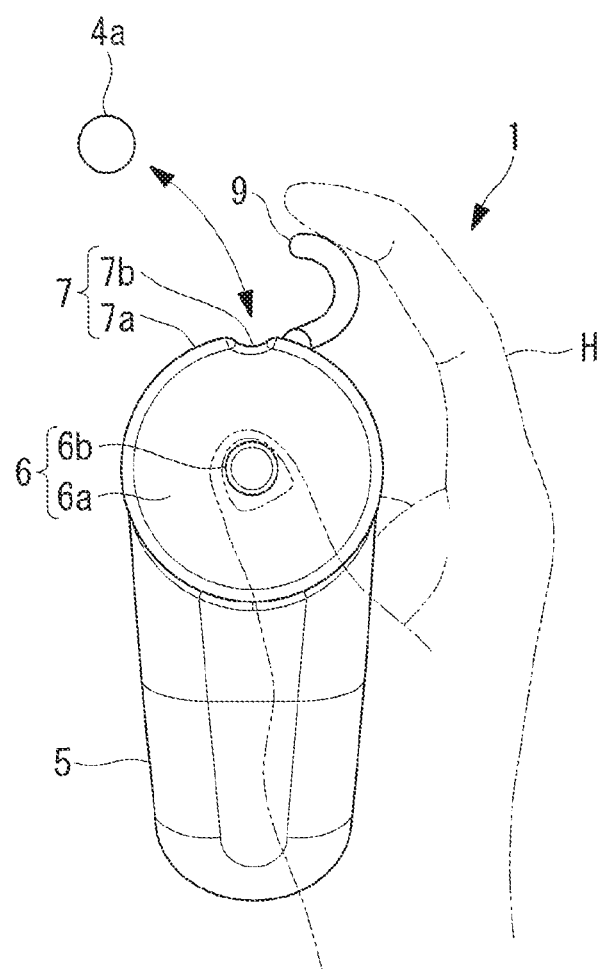
FIG. 8C is a front view of the endoscopic-treatment-instrument operation input device in FIG. 8A and illustrates a state in which a trunk section has been removed.
Figure 9:
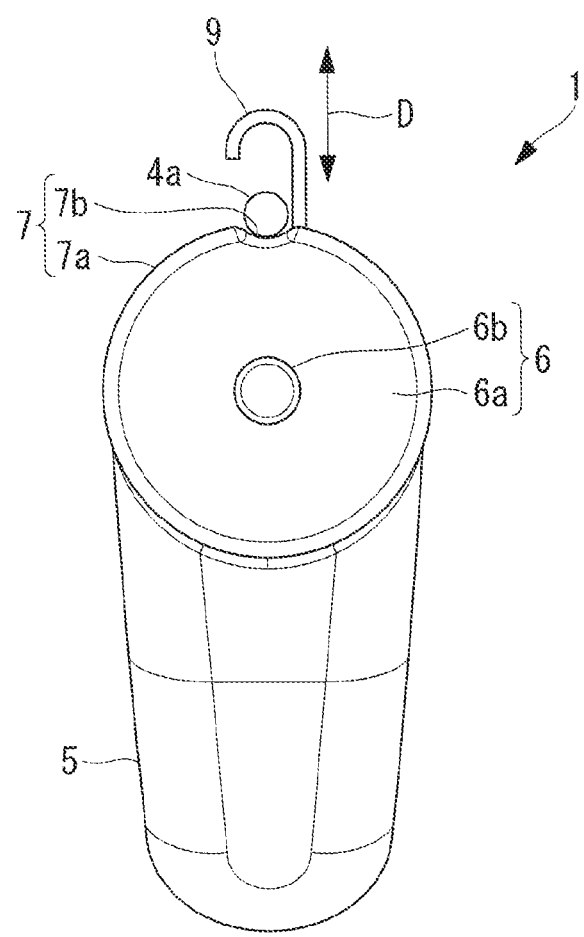
FIG. 9 is a front view illustrating an endoscopic-treatment-instrument operation input device provided with a clamping member that is different from that in FIG. 7A.

The clamping member 9 may be provided on the semi-cylindrical surface 7a so as to be able to swing from the side opposite to the index finger, as illustrated in FIGS. 7A and 7B, or may be provided so as to be able to swing from the side of the index finger, as illustrated in FIGS. 8A to 8C. Furthermore, the clamping member 9 may be provided so to be able to move linearly in the directions of arrows D, as illustrated in FIG. 9.

Figure 10A:
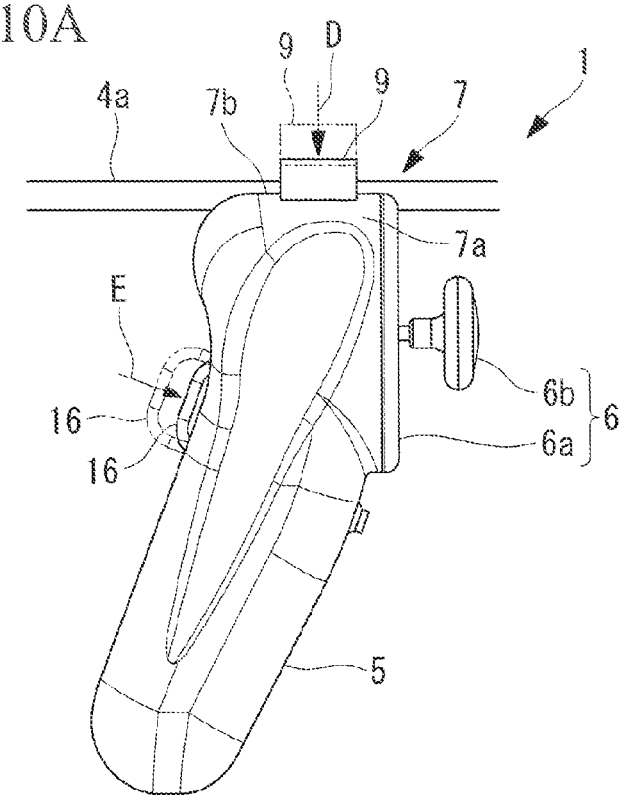
FIG. 10A is a side view illustrating a modification of the endoscopic-treatment-instrument operation input device in FIG. 9.
Figure 10B:
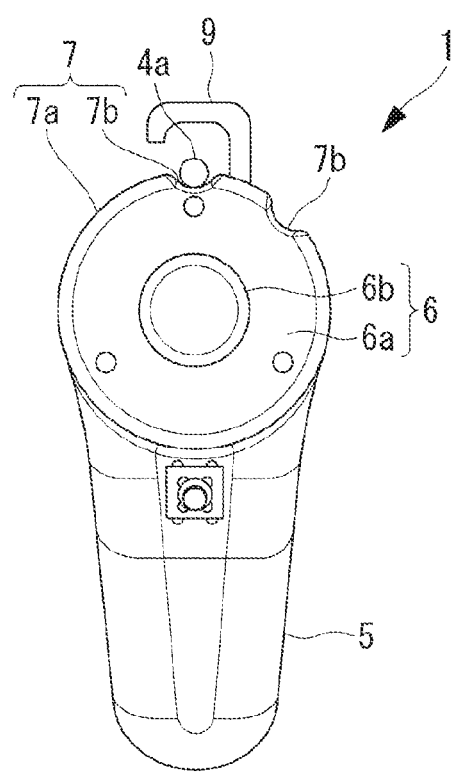
FIG. 10B is a front view of the endoscopic-treatment-instrument operation input device in FIG. 10A.

In addition, rather than the clamping member 9 being moved by being directly pressed by the index finger, a mechanism may be included with which the clamping member 9 can be moved in a direction so as to come closer to the groove 7b and can be made to press the trunk section 4a of the treatment instrument 4 against the groove 7b by pushing a switch 16 provided on a rear surface of the grip section 5 as indicated by an arrow E, as illustrated in FIGS. 10A and 10B.

Figure 11A:
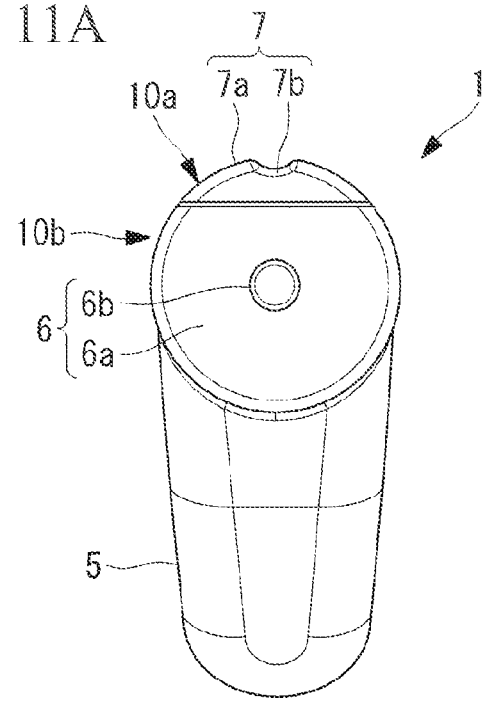
FIG. 11A is a front view of a fourth modification of the endoscopic-treatment-instrument operation input device in FIG. 3A and illustrates a state in which a detachable part has been attached to a device body.
Figure 11B:
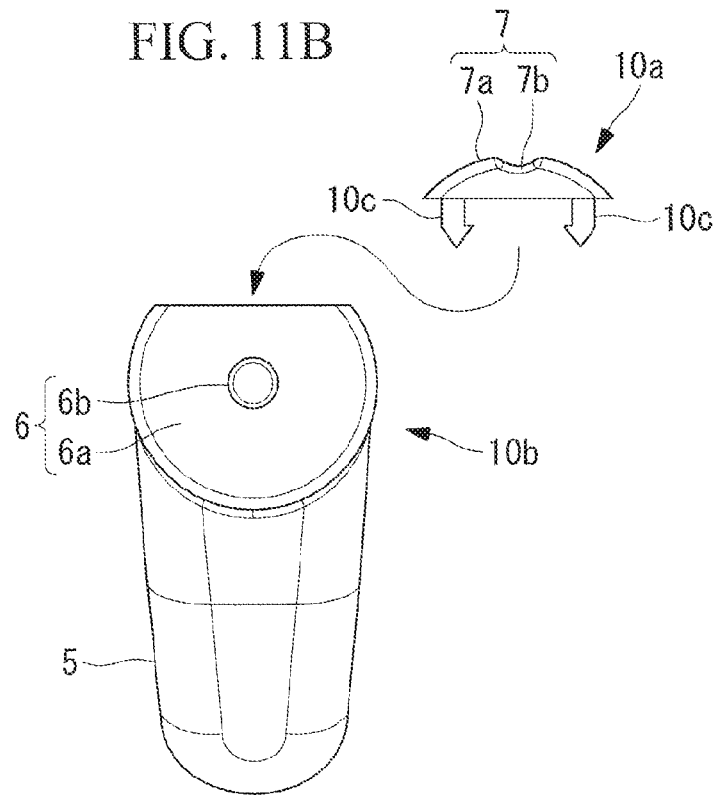
FIG. 11B is a front view of the endoscopic-treatment-instrument operation input device in FIG. 11A and illustrates a state in which the detachable part has been removed from the device body.

Furthermore, as illustrated in FIGS. 11A and 11B, a component (detachable part) 10a that includes the groove 7b of the frictional fixing section 7 may be provided so as to be attachable to and detachable from another component (device body) 10b. With this configuration, the inner diameter of the groove 7b that presses against the trunk section 4a of the treatment instrument 4 can be exchanged for one that is suitable for the outer diameter of the treatment instrument 4. Symbols 10c denote engagement pieces having a snap-fit form or the like for allowing the component 10a to be attached to and detached from the component 10b.

Figure 12:
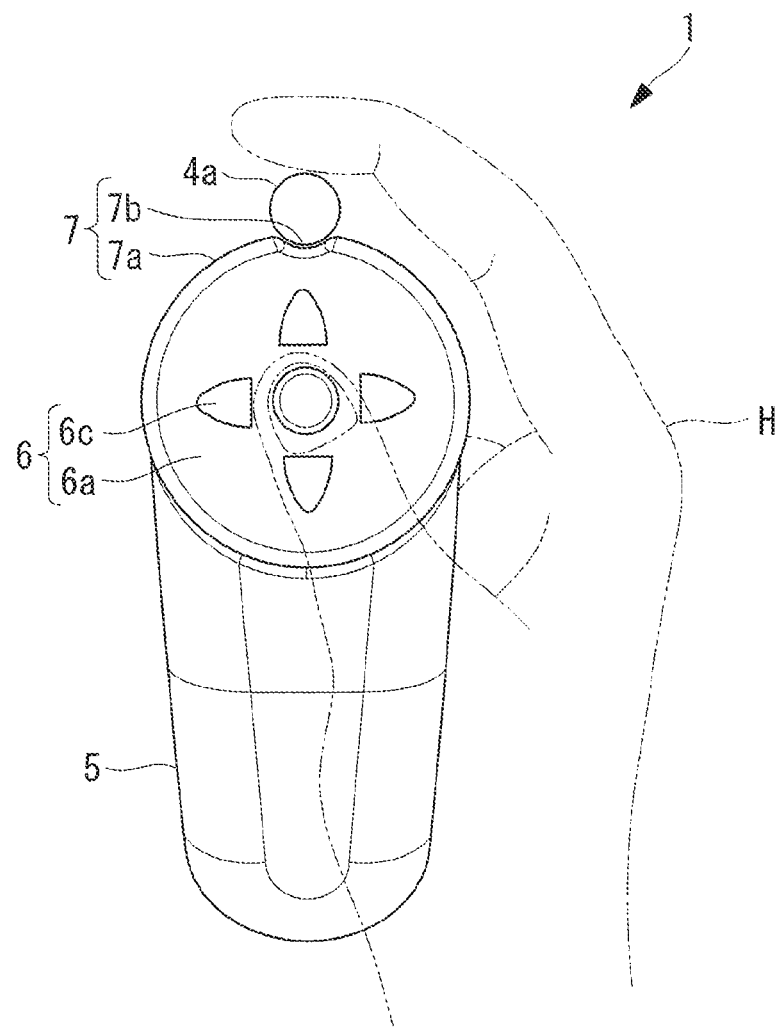
FIG. 12 is a front view illustrating a fifth modification of the endoscopic-treatment-instrument operation input device in FIG. 3A.
Figure 13:
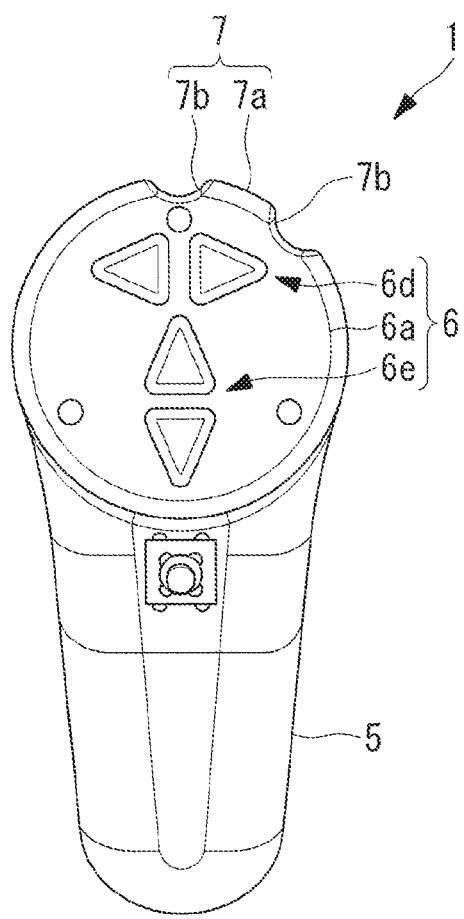
FIG. 13 is a front view illustrating a sixth modification of the endoscopic-treatment-instrument operation input device in FIG. 3A.

In addition, as illustrated in FIG. 12, the operation section 6 may include a cross button 6c instead of the joystick 6b. Furthermore, as illustrated in FIG. 13, a plurality of pairs of forward/backward direction operation buttons (operation members) 6d and 6e may be arranged side-by-side in the longitudinal direction of the thumb of the hand H that grips the grip section 5 for each of the joints 4b and 4c that are arranged side-by-side in the longitudinal direction of the trunk section 4a of the treatment instrument 4 and are able to pivot in directions orthogonal to each other.

By arranging the pairs of operation buttons 6d and 6e so as to correspond to the plurality of joints 4b and 4c arranged side-by-side in the longitudinal direction of the treatment instrument 4, when the operator operates the treatment instrument 4 while looking at the distal end of the treatment instrument 4 displayed on a monitor, the operator can easily associate the actuation directions of the joints 4b and 4c and the operation directions of the operation buttons 6d and 6e with each other and can intuitively cause the joints 4b and 4c to actuate.

Figure 14:
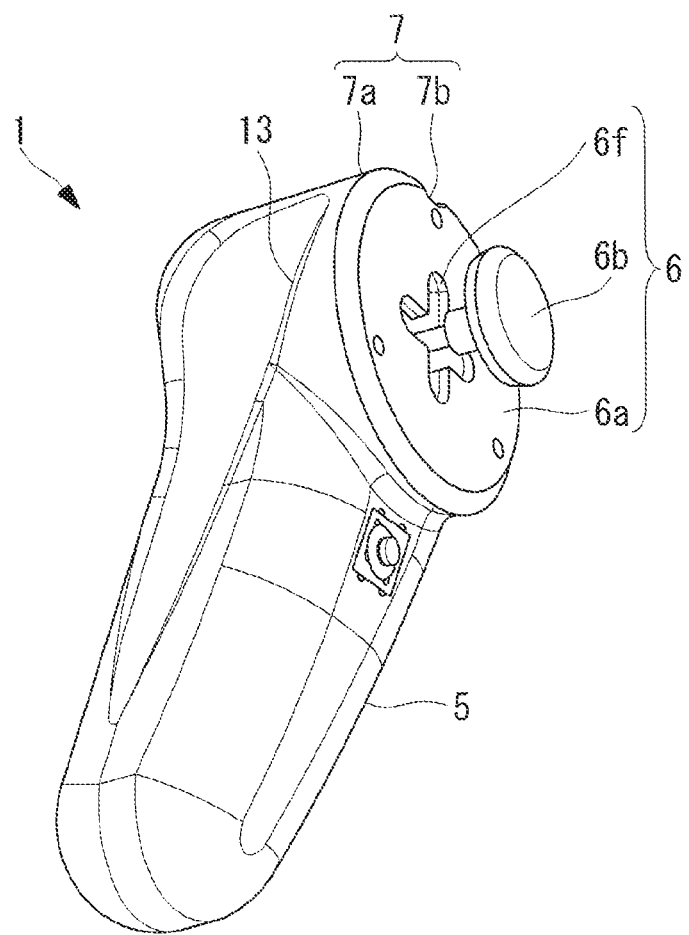
FIG. 14 is a perspective view illustrating a seventh modification of the endoscopic-treatment-instrument operation input device in FIG. 3A.

In addition, as illustrated in FIG. 14, in the case where the plurality of joints 4b and 4c are to be made to actuate with a single joystick (operation member) 6b, tilting directions of the joystick 6b may be restricted by a cross-shaped groove 6f provided in the flat part 6a. Thus, the joints 4b and 4c can be alternately made to actuate by operating the joystick 6b.

Figure 15:
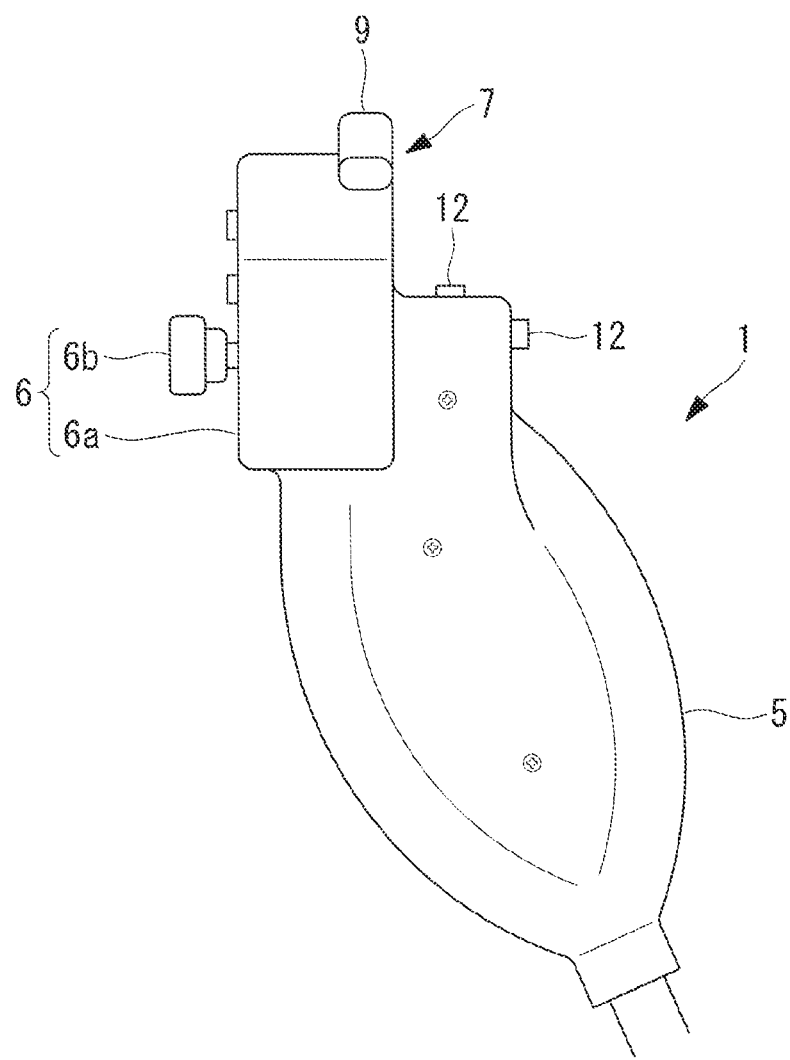
FIG. 15 is a side view illustrating an eighth modification of the endoscopic-treatment-instrument operation input device in FIG. 3A.

Furthermore, the treatment instrument 4 has the end effector 4d at the distal end thereof, and it is desirable that the end effector 4d also be operated using the operation input device 1. In this case, for example, as illustrated in FIG. 15, a switch 12 for the end effector 4d, such as a current passing switch for electrodes of an electric scalpel or a forceps opening/closing switch, may be provided at a position where the middle finger is arranged on the rear side of the grip section 5.

Even in a state where the grip section 5 is gripped by the palm, the little finger, and the ring finger, the trunk section 4a of the treatment instrument 4 is clamped by the index finger, and the operation section 6 is operated by the thumb, the middle finger can be independently moved, and the end effector 4d can be made to function while other operations are being performed. The switch 12 may be provided at a position where the switch 12 can be operated with the index finger when the index finger is free, such as when the clamping member 9 is locked.

Figure 16:
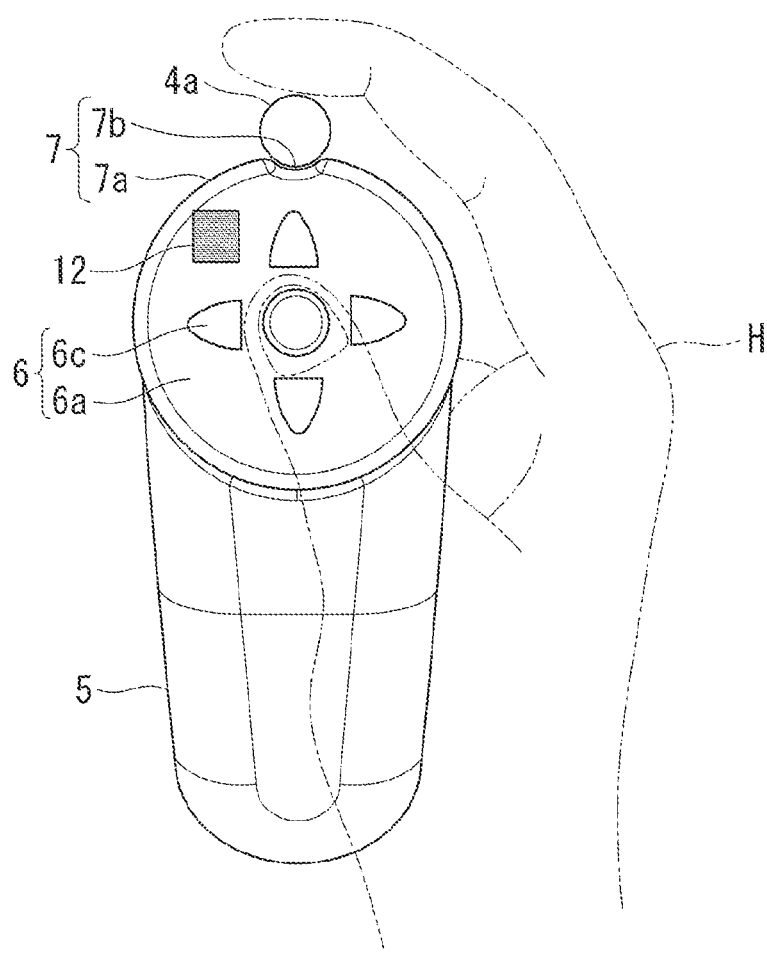
FIG. 16 is a front view illustrating a ninth modification of the endoscopic-treatment-instrument operation input device in FIG. 3A.
Figure 17:
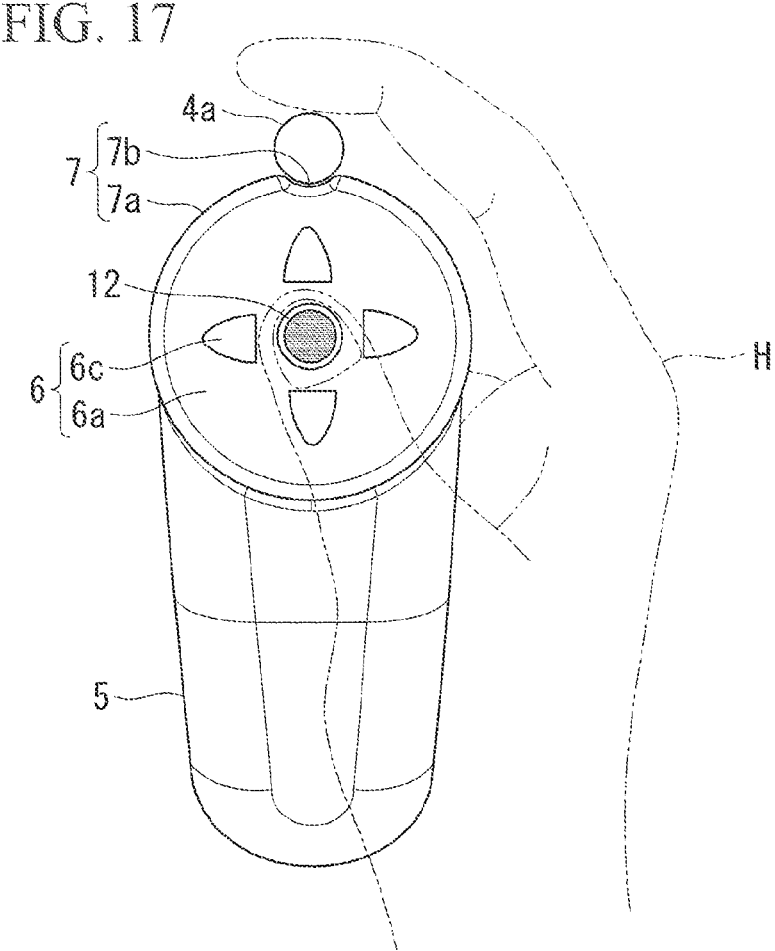
FIG. 17 is a front view illustrating a tenth modification of the endoscopic-treatment-instrument operation input device in FIG. 3A.

As illustrated in FIGS. 16 and 17, the switch 12 of the end effector 4d may be arranged on the flat part 6a of the operation section 6, but there is an advantage to the switch 12 being operated using the middle finger, as illustrated in FIG. 13, in that it is possible to prevent the operation of the switch 12 from being confused with another operation.

Figure 18A:
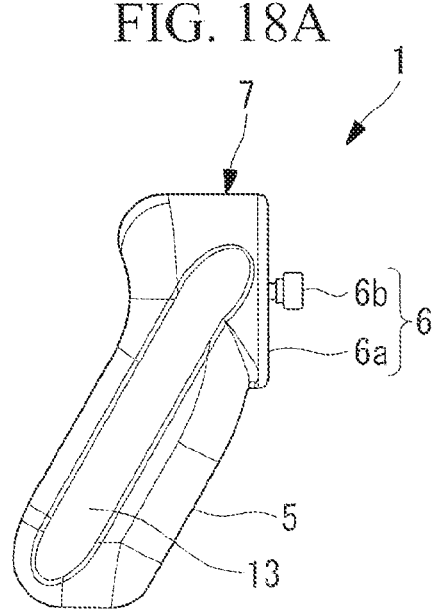
FIG. 18A is a side view illustrating an eleventh modification of the endoscopic-treatment-instrument operation input device in FIG. 3A.

In addition, as illustrated in FIG. 18A, an insertion section accommodating groove 13 may be provided in the side surface of the grip section 5, the insertion section accommodating groove 13 being able to accommodate part of a side surface of the insertion section 2a of the endoscope 2 along the longitudinal direction of the grip section 5.

The inner surface of the insertion section accommodating groove 13 is formed in the shape of the inner surface of a cylinder having an inner diameter that is somewhat larger than the outer diameter of the insertion section 2a. When the operator grips the grip section 5 with the right hand H, it is preferable that the insertion section accommodating groove 13 be for example provided at a position faced by the first joints of the little finger to the middle finger of the right hand H gripping the grip section 5.

Figure 18B:
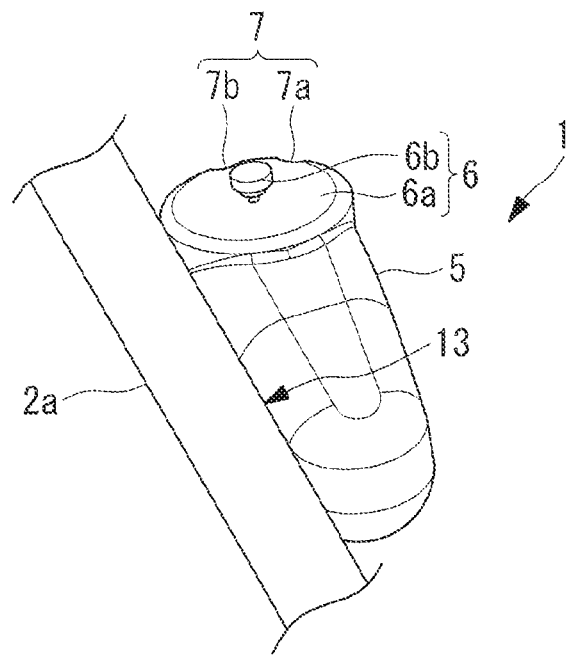
FIG. 18B is a perspective view of the endoscopic-treatment-instrument operation input device in FIG. 18A and illustrates a state in which an insertion section is mounted.
Figure 18C:
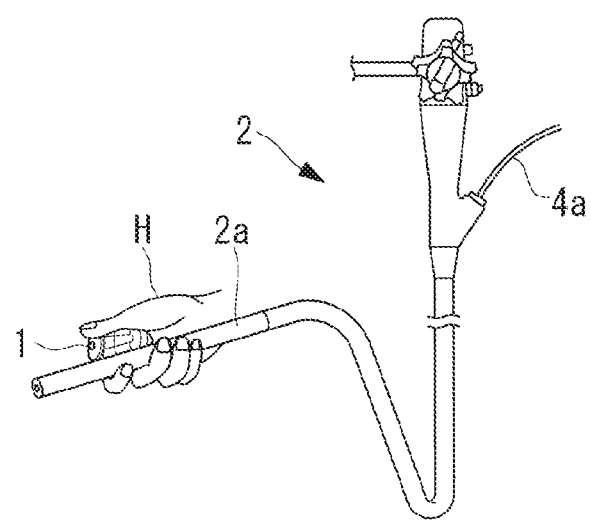
FIG. 18C is an overall view of the endoscopic-treatment-instrument operation input device in FIG. 18A, illustrating a state in which the device is in use.

By adopting this configuration, the side surface of the insertion section 2a can be partially accommodated in the insertion section accommodating groove 13, as illustrated in FIG. 18B, and the grip section 5 and the insertion section 2a can be held so as to be grasped together in three fingers, namely, the little finger to the middle finger of the hand gripping the grip section 5, as illustrated in FIG. 18C. Thus, when it is desired to cause the joints 4b and 4c at the distal end of the treatment instrument 4 to actuate by operating the operation section 6 while adjusting the position of the distal end of the insertion section 2a by performing a forward/backward movement operation along the longitudinal axis of the insertion section 2a or a twisting operation around the longitudinal axis, such an operation can be performed by shifting the gripping hand from the treatment instrument 4 to the insertion section 2a.

Figure 19:
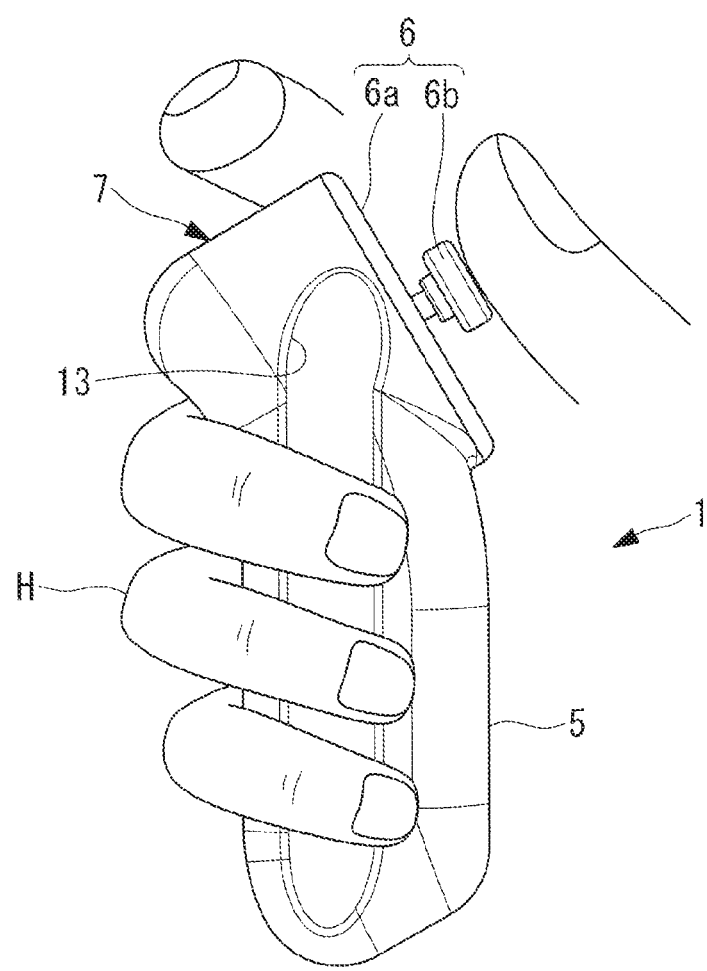
FIG. 19 is a side view for describing the operation of the endoscopic-treatment-instrument operation input device in FIG. 18A.

In addition, as a result of providing the insertion section accommodating groove 13 at such a position, since the grip section 5 is held such that the first joints of the three fingers from the little finger to the middle finger of the hand H gripping the grip section 5 exactly overlap the insertion section accommodating groove 13, as illustrated in FIG. 19, when the insertion section 2a is not gripped there is also an advantage in that the force with which the grip section 5 is gripped when operating the treatment instrument 4 can be increased.

Figure 20A:
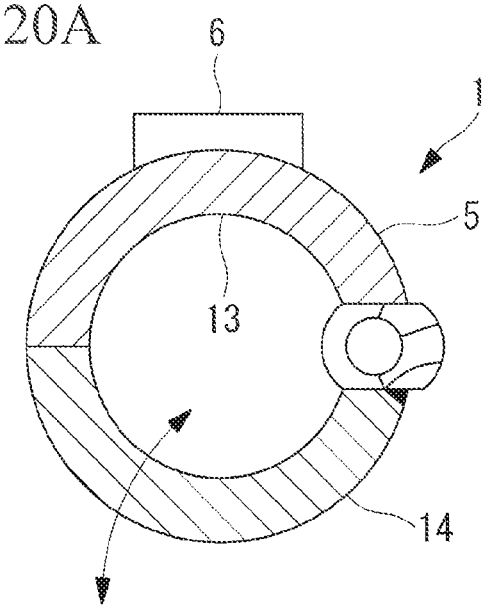
FIG. 20A is a longitudinal sectional view illustrating a twelfth modification of the endoscopic-treatment-instrument operation input device in FIG. 3A.
Figure 20B:
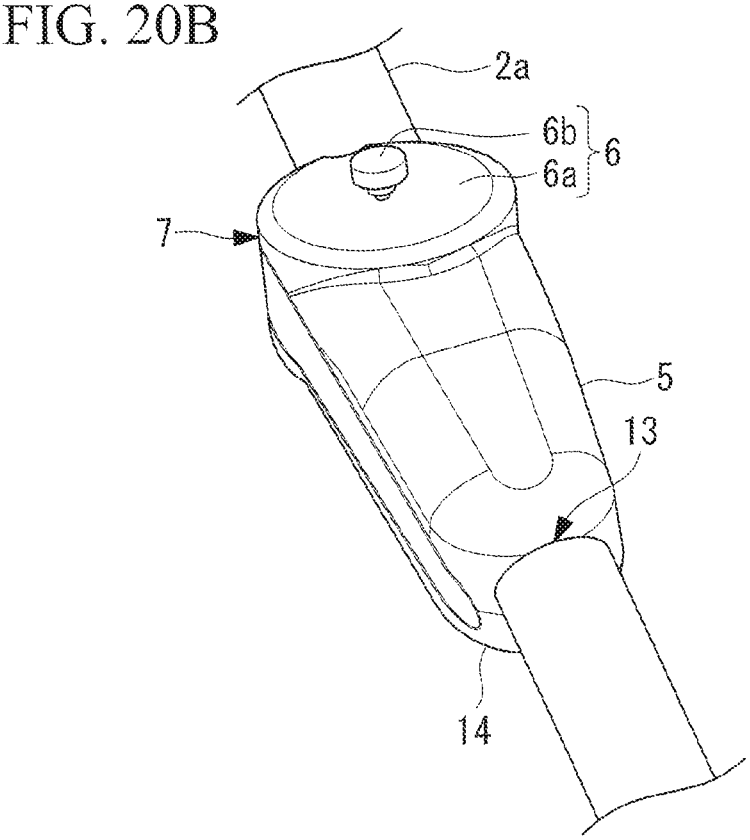
FIG. 20B is a perspective view of the endoscopic-treatment-instrument operation input device in FIG. 20A and illustrates a state in which an insertion section is mounted.

Furthermore, as a structure for fixing the operation input device 1 to the insertion section 2a, it is permissible to adopt a structure that includes the insertion section accommodating groove 13 that is provided so as to extend along the longitudinal direction of the grip section 2, as illustrated in FIG. 20A, and a clamping member 14 that is provided so as to open and close with respect to the insertion section accommodating groove 13 and, as illustrated in FIG. 20B, clamps the insertion section 2a in a radial direction against the insertion section accommodating groove 13 in a closed state.

In addition, in this embodiment, the frictional fixing section 7, which fixes the treatment instrument 4 in place, may be provided with a sensor (not illustrated) that detects whether the treatment instrument 4 is being pressed thereagainst. In the case where the sensor detects that the treatment instrument 4 is not in contact therewith, functioning of the treatment instrument 4 can be stopped, and an operation performed by the operation section 6 can be nullified. Furthermore, forward/backward movement and twisting of the treatment instrument 4 may be locked. A contact sensor, an infrared sensor or a switch may be used as the sensor. Thus, the operator can be prevented from performing an unintended operation.

In addition, in this embodiment, the grip section 5 may be provided with a sensor (not illustrated) that detects whether the grip section 5 is being gripped by an operator. In the case where the sensor detects that the grip section 5 is not being gripped, functioning of the treatment instrument 4 can be stopped and an operation performed by the operation section 6 can be nullified. Furthermore, forward/backward movement and twisting of the treatment instrument 4 may be locked. A contact sensor, an infrared sensor or a switch may be used as the sensor. Thus, the operator can be prevented from performing an unintended operation.

Furthermore, in this embodiment, although a case in which an operator grips the grip section 5 with the right hand H was exemplified and described, a configuration may instead be adopted in which an operator grips the grip section 5 with the left hand H. In addition, the grip section 5 may be formed so as to be symmetrical such that the grip section 5 can be gripped by either of the left and right hands H.

The above-described embodiment is derived from the individual aspects of the present invention below.

An aspect of the present invention is an endoscopic-treatment-instrument operation input device for operating a treatment instrument that has a joint at a distal end of elongated trunk section to be introduced via a channel of an endoscope, the operation input device including: a grip section shaped so as to be capable of being gripped by a palm and at least a little finger and a ring finger of one hand of an operator; an operation section that is arranged at a position so as to be operable by a thumb of the gripping hand in a state where the grip section is being gripped and that allows an operation command for causing the joint to actuate to be input; and a frictional fixing section that presses, and fixes in place with friction, the trunk section at a position midway along the trunk section in a longitudinal direction of the trunk section through use of an index finger of the gripping hand in a state where the grip section is being gripped.

According to this aspect, the operator can fix the operation section to the trunk section of the treatment instrument by gripping the grip section with the palm and at least the little finger and ring finger of one hand and pressing a position midway along the trunk section of the treatment instrument in the longitudinal direction against the frictional fixing section by using the index finger of the gripping hand. Thus, the operator grips the trunk section of the treatment instrument in the vicinity of an insertion opening into the channel of the endoscope and can consequently apply a pushing/pulling force and a twisting force at a position not at the base end of the trunk section but rather midway along the trunk section in the longitudinal direction similarly to as with a conventional hand-operated treatment instrument. Therefore, the operation efficiency of a doctor who is used to conventional endoscope techniques can be improved and operational forces can be transferred with more certainty to the distal end of the endoscope.

In a state where the trunk section of the treatment instrument is being operated, the operation section, which is fixed to the trunk section, can be operated by using the thumb, which is free, of the hand gripping the grip section and the joint provided at the distal end of the treatment instrument can be caused to actuate with an operation command input from the operation section.

In the above-described aspect, the frictional fixing section may be provided with a groove at a position that faces the index finger of the hand gripping the grip section, the groove extending in a direction that intersects a length direction of the index finger and being capable of closely contacting a side surface of the trunk section.

With this configuration, when the trunk section of the treatment instrument is accommodated inside the groove, the index finger of the hand gripping the grip section is arranged so as to intersect the longitudinal direction of the treatment instrument. Therefore, the trunk section of the treatment instrument is clamped between the index finger and the groove by the force applied by the index finger, and as a result the trunk section can be supported so as to not fall out of the groove, and the side surface of the trunk section can be easily made to closely contact and be fixed against the inner surface of the groove. Thus, the trunk section of the treatment instrument is fixed to the operation section in the longitudinal direction of the trunk section through friction with the inner surface of the groove, is also fixed to the operation section in a width direction of the groove as a result of being accommodated inside the groove, and is fixed so as not to come out of the groove by being pressed by the index finger.

In the above-described aspect, a plurality of the grooves may be provided so as to be spaced apart from each other in a circumferential direction.

With this configuration, it is possible to select a groove in which to accommodate the trunk section of the treatment instrument in accordance with individual differences between operators such as index finger length or ease of pressing.

In the above-described aspect, the groove may extend in a direction that intersects a direction of an operation performed by the thumb on the operation section.

With this configuration, a joint operation in which the joint pivots around an axis intersecting the longitudinal direction of the trunk section of the treatment instrument can be performed by moving the thumb in an operation direction that intersects the longitudinal direction of the trunk section of the treatment instrument accommodated inside the groove and the operator can intuitively operate the joint.

In the above-described aspect, the groove may be formed in the shape of an inner surface of a cylinder having an inner diameter that is larger than an outer diameter of the trunk section.

With this configuration, the trunk section can be accommodated inside the groove, excessive concentration of pressure at the side surfaces of the groove does not occur, and the integrity of the trunk section can be maintained due to the surface of the trunk section being made to closely contact the inner surface of the groove.

The above-described aspect may further include a clamping member that is provided so as to be able to change a relative distance between the clamping member and the frictional fixing section and that clamps in a radial direction the trunk section against the frictional fixing section by being moved by the index finger of the hand gripping the grip section.

With this configuration, instead of the trunk section of the treatment instrument being directly pressed by the index finger, the trunk section of the treatment instrument is clamped between the clamping member and the frictional fixing section by moving the clamping member closer to the frictional fixing section, and as a result the trunk section can be pressed against the frictional fixing section with more certainty, and a stable operation can be carried out with the treatment instrument.

The above-described aspect may further include an urging member that urges the clamping member in a direction away from the frictional fixing section.

With this configuration, the pressing force applied to the clamping member from the index finger is removed, and consequently, the clamping member is separated from the frictional fixing section by the urging member, and therefore fixing of the operation section and the trunk section of the treatment instrument to each other can be easily released.

In the above-described aspect, the grip section may be provided with an insertion section accommodating groove that extends in a direction in which the little finger and the ring finger of the hand gripping the grip section are adjacent to each other and that fixes in place, though friction, a side surface of an insertion section of the endoscope at a position midway along the insertion section in a longitudinal direction by allowing the side surface to closely contact the insertion section accommodating groove.

In this configuration, the trunk section of the treatment instrument that was fixed to the frictional fixing section by the index finger is released, and instead the side surface of the insertion section of the endoscope is made to closely contact the insertion section accommodating groove, the grip section is gripped, and the side surface of the insertion section is pressed against the insertion section accommodating groove by using at least the little finger and the ring finger, and consequently the insertion section and the operation section can be fixed to each other with friction. Thus, the joint of the treatment instrument can be made to actuate by operating the operation section by using the thumb while performing an operation of pushing or pulling the insertion section in the longitudinal direction or an operation of twisting the insertion section around the longitudinal axis.

In above-described aspect, the operation section may be provided with a substantially flat operation surface and an operation member that is arranged on the operation surface and is operated with the thumb, the insertion section accommodating groove and the operation surface intersecting to form an acute angle therebetween.

With this configuration, when the operation section is operated while observing the distal end of the treatment instrument on a monitor, it is possible to associate the operation directions of the operation member and the articulation directions of the joint of the treatment instrument with each other and perform an operation without there being a feeling of unnaturalness.

In the above-described aspect, the grip section may be provided with an insertion section clamping body that is provided so as to be able to change a relative distance between the insertion section clamping body and the insertion section accommodating groove and that clamps, in a radial direction, the insertion section against the insertion section accommodating groove by being moved toward the insertion section accommodating groove.

With this configuration, the insertion section and the operation section can be fixed to each other with friction by moving the insertion section clamping body away from the insertion section accommodating groove, arranging the insertion section between the insertion section clamping body and the insertion section accommodating groove, and then clamping the insertion section between the insertion section clamping body and the insertion section accommodating groove by moving the insertion section clamping body toward the insertion section accommodating groove.

In the above-described aspect, the insertion section accommodating groove may be arranged at a position substantially facing first joints of the little finger and the ring finger of the hand gripping the grip section.

With this configuration, when the insertion section of the endoscope is arranged in the insertion section accommodating groove, the insertion section can be gripped together with the grip section by using the little finger and the ring finger of the hand gripping the grip section. On the other hand, when the insertion section is not arranged in the insertion section accommodating groove, the grip section can be firmly gripped by hooking the first joints of the little finger and the ring finger onto the insertion section accommodating groove.

In the above-described aspect, the grip section may be provided with an operation switch that is arranged at a position facing the middle finger of the hand gripping the grip section.

With this configuration, the operation switch can be operated with the middle finger, which is free, in a state where the grip section is gripped between the little finger, the ring finger and the palm, the operation section is fixed to the trunk section of the treatment instrument by the index finger and the joint at the distal end of the treatment instrument is operated with the thumb. For example, a switch that turns on or off the supply of electricity to electrodes provided in the treatment instrument or a switch that turns on or off electrical driving of a treatment instrument joint can be used as the operation switch.

The above-described aspect may further include a sensor that detects at least one of a gripping state at the grip section and a fixing state at the frictional fixing section.

With this configuration, gripping of the grip section by the hand of the operator or a fixing state of the trunk section of the treatment instrument in the frictional fixing section is detected by the sensor. Therefore, in the case where it is detected that the grip section is not being gripped by the hand of the operator or that the trunk section of the treatment instrument is not fixed to the frictional fixing section, the detection result can be used for example in processing to ensure that the treatment instrument does not function even if the operation section is operated.

In the above-described aspect, a plurality of the joints of the treatment instrument may be arranged in the longitudinal direction of the trunk section, the operation section may be provided with a plurality of the operation members for causing the joints to actuate, and the operation members may be arranged in a longitudinal direction of the thumb of the hand gripping the grip section.

With this configuration, the thumb of the hand gripping the grip section is moved in the longitudinal direction of the thumb and the operation members, which are arranged at different positions in the longitudinal direction of the thumb, are operated, whereby the plurality of joints arranged in the longitudinal direction of the trunk section can be intuitively actuated.

In the above-described aspect, a plurality of pairs of forward/backward direction operation members may be provided in the same number as the number of the joints of the treatment instrument, and the pairs of operation members may be arranged in the same order as the joints with respect to a longitudinal axis of the trunk section.

With this configuration, when the operation section is operated while observing the distal end of the treatment instrument on a monitor, it is possible to associate the joints of the treatment instrument and the articulation directions of the joints with the operation members corresponding to the joints and the operation directions of the operation members and intuitively perform an operation without there being a feeling of unnaturalness.

In the above-described aspect, a plurality of the joints of the treatment instrument may be arranged in the longitudinal direction of the trunk section, the operation section may be provided with a single operation member for causing the joints to actuate, and the operation member may be provided so as to be selectively movable in directions that correspond to actuation directions of the joints of the treatment instrument.

With this configuration, the joints can be made to actuate individually by simply operating the single operation member in the directions corresponding to the actuation directions of the joints, and intuitive operations can be performed while observing the distal end of the treatment instrument on a monitor.

The above-described aspect may further include a device body provided with the grip section and the operation section; and a detachable part that can be attached to and detached from the device body and that is provided with the frictional fixing section.

With this configuration, once a treatment has been performed by attaching the detachable part provided with the frictional fixing section to the device body and fixing the trunk section of the treatment instrument to the frictional fixing section, the detachable part, which has contacted the treatment instrument, can be removed and replaced. Thus, a frictional fixing section that is appropriate for the shape of the trunk section of the treatment instrument to be used can be mounted by replacing just the detachable part and operability can be improved. In addition, by replacing only the detachable part after using the operation input device, the treatment instrument can be fixed to a frictional fixing section that is in a very clean state and the device body can be reused.

REFERENCE SIGNS LIST

H right hand (one hand)
1 operation input device (endoscopic-treatment-instrument operation input device)
2 endoscope
3 instrument channel (channel)
4 treatment instrument
4a trunk section
4b, 4c joint
4d end effector
5 grip section
6 operation section
6d, 6e operation button (operation member)
7 frictional fixing section
7b groove
9 clamping member
10a component (device body)
10b component (detachable part)
12 operation switch
13 insertion section accommodating groove
14 clamping member (insertion section clamping body)

The invention claimed is:

1. An endoscopic-treatment-instrument operation input device for operating a treatment instrument having a joint at a distal end of an elongated trunk section to be introduced via a channel of an endoscope, the operation input device comprising:
a body, the body comprising:
a grip section shaped so as to be gripped by a hand of an operator, the grip section extending along a first longitudinal axis;
a joystick positioned on a planar surface of the body so as to be operable by a thumb of the hand in a state where the grip section is being gripped, the joystick being operated to generate an operation command for causing the joint to actuate; and
a groove positioned on an external surface of the body, the groove extending along a second longitudinal axis, the second longitudinal axis being non-parallel to the first longitudinal axis, the groove being configured to receive a portion of the trunk section therein and an index finger of the hand is pressed against the portion of the trunk section to retain the trunk section within the groove in a state where the grip section is being gripped by the hand;
wherein the first longitudinal axis of the grip section intersects with the planar surface of the body and the second longitudinal axis of the groove; and
the groove is positioned on a portion of the body other than the grip section and the joystick is positioned between the groove and the grip section.

2. The endoscopic-treatment-instrument operation input device according to claim 1, wherein the groove is disposed at a position of the body that faces the index finger of the hand in the state where the grip section is being gripped.

3. The endoscopic-treatment-instrument operation input device according to claim 2, wherein the groove comprises a plurality of grooves arranged on the external surface of the body so as to be spaced apart from each other in a direction offset from the first longitudinal axis.

4. The endoscopic-treatment-instrument operation input device according to claim 2, wherein the joystick being configured such that the thumb is oriented in an operation direction to operate the joystick, the groove extending in a direction that intersects the operation direction.

5. The endoscopic-treatment-instrument operation input device according to claim 2, wherein the groove is formed in the shape of an inner surface of a cylinder, the groove having an inner diameter that is larger than an outer diameter of the trunk section.

6. The endoscopic-treatment-instrument operation input device according to claim 1, further comprising a clamping member arranged movably on the body, the clamping member being configured to change a relative distance between the clamping member and the groove, the clamping member clamping, in a radial direction, the trunk section against the groove by being moved by the index finger of the hand gripping the grip section.

7. The endoscopic-treatment-instrument operation input device according to claim 6, further comprising an urging member that urges the clamping member in a direction away from the groove.

8. The endoscopic-treatment-instrument operation input device according to claim 6, further comprising:
a trigger member provided on a rear surface side of the grip section with respect to the joystick, the trigger member being operated by the index finger of the hand gripping the grip section; and
an interlocking mechanism that changes the relative distance of the joystick from the groove in accordance with operation of the trigger member.

9. The endoscopic-treatment-instrument operation input device according to claim 1, wherein the grip section comprises an insertion section accommodating groove extending in a grip direction in which a little finger and a ring finger of the hand gripping the grip section are adjacent to each other and that fixes in place through friction a side surface of an insertion section of the endoscope at a position along the insertion section in a longitudinal direction of the insertion section by allowing the side surface to closely contact the insertion section accommodating groove.

10. The endoscopic-treatment-instrument operation input device according to claim 9, wherein:
the insertion section accommodating groove and the planar surface intersect forming an acute angle therebetween.

11. The endoscopic-treatment-instrument operation input device according to claim 10, wherein the grip section comprises an insertion section clamping body provided so as to be able to change a relative distance between the insertion section clamping body and the insertion section accommodating groove, the insertion section clamping body clamping, in a radial direction, the insertion section against the insertion section accommodating groove by being moved toward the insertion section accommodating groove.

12. The endoscopic-treatment-instrument operation input device according to claim 11, wherein the insertion section accommodating groove is positioned to substantially face first joints of the little finger and the ring finger of the hand gripping the grip section.

13. The endoscopic-treatment-instrument operation input device according to claim 1, wherein the grip section comprises an operation switch positioned to face the middle finger of the hand gripping the grip section.

14. The endoscopic-treatment-instrument operation input device according to claim 1, further comprising a sensor configured to detect at least one of a gripping state at the grip section and a fixing state at the groove.

15. The endoscopic-treatment-instrument operation input device according to claim 1, wherein:
the joint comprises a plurality of joints arranged in a longitudinal direction of the trunk section,
the joystick comprises a plurality of joysticks for causing the plurality of joints to actuate, and
the plurality of joysticks are arranged in a longitudinal direction of the thumb of the hand gripping the grip section.

16. The endoscopic-treatment-instrument operation input device according to claim 15, wherein:
a plurality of pairs of forward/backward direction joysticks are provided in a same number as a number of the plurality of joints of the treatment instrument, and
the plurality of pairs of the joysticks are arranged in a same order as the plurality of joints with respect to a longitudinal axis of the trunk section.

17. The endoscopic-treatment-instrument operation input device according to claim 1, wherein:
the joint comprises a plurality of joints arranged in a longitudinal direction of the trunk section,
the joystick causes the plurality of joints to actuate, and
the joystick is provided so as to be selectively movable in directions that correspond to actuation directions of the plurality of joints of the treatment instrument.

18. The endoscopic-treatment-instrument operation input device according to claim 1, further comprising
a detachable part that can be attached to and detached from the body, the detachable part being provided with the groove.

19. The endoscopic-treatment-instrument operation input device according to claim 1, wherein the planar surface of the body is inclined with respect to the first longitudinal axis of the grip section.

20. The endoscopic-treatment-instrument operation input device according to claim 1, wherein the second longitudinal axis of the groove is substantially parallel to a longitudinal axis of the joystick.

21. The endoscopic-treatment-instrument operation input device according to claim 1, wherein the planar surface of the body is substantially normal to the second longitudinal axis of the groove.

22. An endoscopic-treatment-instrument operation input device for operating a treatment instrument having a joint at a distal end of an elongated trunk section of the treatment instrument, the trunk section being introduced via a channel of an endoscope, the operation input device comprising:
a body, the body comprising:
a grip section shaped so as to be gripped by a hand of an operator, the grip section extending along a first longitudinal axis;
a joystick positioned on a planar surface of the body so as to be operable by a thumb of the hand in a state where the grip section is being gripped, the joystick being operated to generate an operation command for causing the joint of the treatment instrument to actuate; and
a groove positioned on an external surface of the body, the groove extending along a second longitudinal axis, the second longitudinal axis being non-parallel to the first longitudinal axis, the groove being configured to receive a portion of the trunk section therein and an index finger of the hand is pressed against the portion of the trunk section to retain the trunk section within the groove in a state where the grip section is being gripped by the hand;
wherein the first longitudinal axis of the grip section intersects with the planar surface of the body and the second longitudinal axis of the groove; and
the groove being positioned on a portion of the body other than the grip section.

23. The endoscopic-treatment-instrument operation input device according to claim 22, wherein:
the groove comprises a first groove; and
the endoscopic-treatment-instrument operation input device further comprising a second groove, wherein the second groove having a longitudinal axis along an external surface of the body, the longitudinal axis of the second groove being offset from the first longitudinal axis of the grip section.

24. The endoscopic-treatment-instrument operation input device according to claim 22, wherein a longitudinal axis of the joystick is positioned on the body to intersect the first longitudinal axis of the grip section.

25. The endoscopic-treatment-instrument operation input device according to claim 22, wherein the planar surface of the body is inclined with respect to the first longitudinal axis of the grip section.

26. The endoscopic-treatment-instrument operation input device according to claim 22, wherein the second longitudinal axis of the groove is substantially parallel to a longitudinal axis of the joystick.

27. The endoscopic-treatment-instrument operation input device according to claim 22, wherein the planar surface of the body is substantially normal to the second longitudinal axis of the groove.

* * * * *